US011383081B2

(12) United States Patent
Ma et al.

(10) Patent No.: US 11,383,081 B2
(45) Date of Patent: Jul. 12, 2022

(54) NEUROSTIMULATION SYSTEM AND METHOD FOR MODULATING ABNORMAL MOTOR MOVEMENT

(71) Applicant: City University of Hong Kong, Kowloon (HK)

(72) Inventors: Chi Him Eddie Ma, Kowloon (HK); Chung Tin, Kowloon (HK); Gajendra Kumar, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 16/454,121

(22) Filed: Jun. 27, 2019

(65) Prior Publication Data

US 2020/0406031 A1  Dec. 31, 2020

(51) Int. Cl.
*A61N 1/36* (2006.01)
*A61N 1/05* (2006.01)
*A61B 5/11* (2006.01)
*A61B 5/24* (2021.01)
*A61B 5/389* (2021.01)
*A61B 5/00* (2006.01)

(52) U.S. Cl.
CPC ........ *A61N 1/36003* (2013.01); *A61B 5/0031* (2013.01); *A61B 5/112* (2013.01); *A61B 5/24* (2021.01); *A61B 5/389* (2021.01); *A61B 5/6847* (2013.01); *A61N 1/0534* (2013.01); *A61N 1/36139* (2013.01); *A61B 2503/40* (2013.01)

(58) Field of Classification Search
CPC ............ A61N 1/36003; A61N 1/36067; A61B 5/04001; A61B 5/0488; A61B 5/0031
See application file for complete search history.

(56) References Cited

U.S. PATENT DOCUMENTS

| 6,301,492 | B1 | 10/2001 | Zonenshayn |
| 6,539,263 | B1 | 3/2003 | Schiff et al. |
| 7,894,903 | B2 | 2/2011 | John |
| 8,280,516 | B2 | 10/2012 | Graupe |
| 9,220,458 | B2 | 12/2015 | Pouratian |
| 9,248,280 | B2 | 2/2016 | Moffitt et al. |
| 9,433,789 | B2 | 9/2016 | Perryman |
| 2007/0162086 | A1* | 7/2007 | DiLorenzo ........... A61B 5/4082 607/45 |

(Continued)

FOREIGN PATENT DOCUMENTS

| CN | 104399181 | 3/2015 | |
| CN | 106413803 | 2/2017 | |
| WO | WO-2004062470 A2 * | 7/2004 | ......... A61N 1/36071 |

*Primary Examiner* — Brian T Gedeon
*Assistant Examiner* — Joshua Andrew Schum-Houck
(74) *Attorney, Agent, or Firm* — Renner Kenner Greive Bobak Taylor & Weber

(57) ABSTRACT

A neurostimulation system includes an electromyographic (EMG) electrode; a neural electrode implantable in a deep cerebellar nuclei of a subject; a data acquisition unit in communication with the EMG electrode for receiving and transmitting a EMG signal; and a processor in communication with the data acquisition unit, the processor generates a EMG pattern based on the EMG signal and outputs a stimulation signal to the neural electrode when the EMG pattern is indicative of an abnormal motor movement. A method of modulating an abnormal motor movement of a subject by using the neurostimulation system.

15 Claims, 12 Drawing Sheets

(56) References Cited

U.S. PATENT DOCUMENTS

| | | | | |
|---|---|---|---|---|
| 2008/0208284 A1* | 8/2008 | Rezai | ................ | A61N 1/36071 |
| | | | | 607/45 |
| 2013/0338726 A1* | 12/2013 | Machado | ........... | A61N 1/36025 |
| | | | | 607/45 |
| 2014/0005743 A1* | 1/2014 | Giuffrida | ........... | A61N 1/36067 |
| | | | | 607/45 |
| 2016/0121110 A1* | 5/2016 | Kent | ................. | A61N 1/36067 |
| | | | | 607/45 |
| 2017/0165481 A1* | 6/2017 | Menon | ............... | A61N 1/36003 |

* cited by examiner

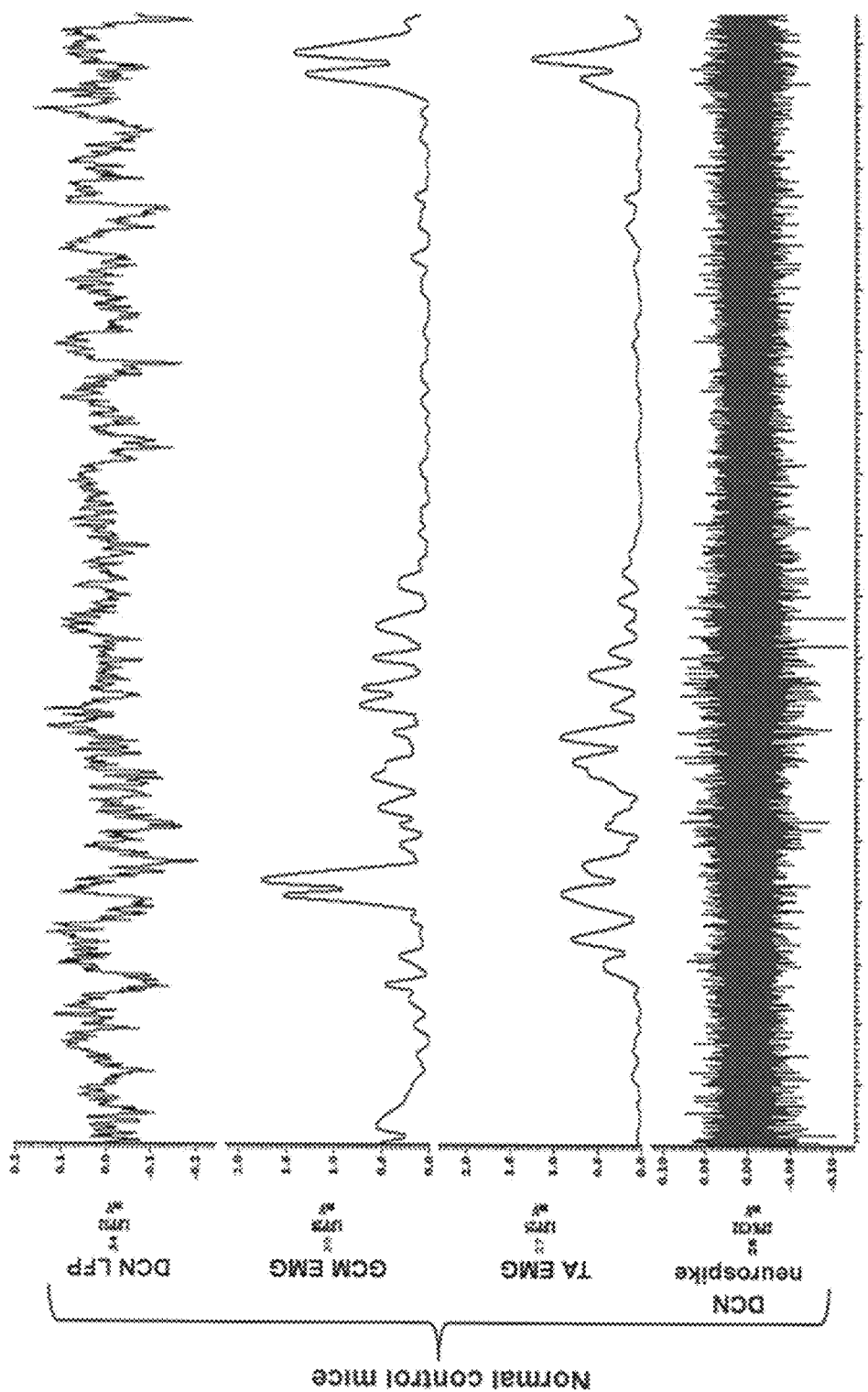

NEUROSTIMULATION SYSTEM AND METHOD FOR MODULATING ABNORMAL MOTOR MOVEMENT

TECHNICAL FIELD

The present invention relates to a neurostimulation system and a method for modulating abnormal locomotion, particularly but not exclusively for modulating abnormal motor movement associated with neurodegenerative diseases.

BACKGROUND OF THE INVENTION

People suffering from neurological disorders may have difficulties in balancing, moving, coordination, speech, logical thinking and the like. Ataxia is one of the neurological disorders which is typically correlated to neurodegeneration. People affected by ataxia have problems with coordination and balance, for example some may struggle to walk in a straight line or become clumsy. There are various types of ataxia including Friedreich's ataxia, gluten ataxia, episodic ataxia and spinocerebellar ataxias.

Spinocerebellar ataxia (SCA) is generally characterized by loss of body balance and motor coordination, speech and oculomotor difficulties. The condition affects 5 in every 100,000 people worldwide, and is incurable. Although there are some treatments to help relieve the symptoms associated with SCA, the existing treatments and devices may provide prolonged stimulation of the entire brain area in patients which may result in increased risks of adverse side effects. Also, the continuous stimulation by the pulse generator significantly reduces the battery life of the device and therefore requires frequent replacement of the device.

Accordingly, there remains a strong need for a novel system and method which have application in the modulation of the abnormal or unstable motor movement particularly in a subject suffering from a neurodegenerative disorder.

SUMMARY OF THE INVENTION

In one aspect, the present invention pertains to a neurostimulation system comprising
an electromyographic (EMG) electrode;
a neural electrode implantable in a deep cerebellar nuclei of a subject;
a data acquisition unit in communication with the EMG electrode for receiving and transmitting a EMG signal; and
a processor in communication with the data acquisition unit, the processor generates a EMG pattern based on the EMG signal and outputs a stimulation signal to the neural electrode when the EMG pattern is indicative of an abnormal locomotion.

In an embodiment, the processor includes a field-programmable gate array.

In an embodiment, the data acquisition unit is in communication with the neural electrode for recording neuronal activity of a subject during a gait movement.

In an embodiment, the processor generates a gait cycle based on the EMG pattern and optionally neuronal activity recorded by the neural electrode. In particular, the processor compares the gait cycle with pre-set gait cycle data to determine whether the EMG pattern is indicative of the abnormal locomotion.

In an embodiment, the data acquisition unit communicates with the processor via a wireless network.

In an embodiment, the processor outputs the stimulation signal to the neural electrode via a stimulus generator.

In an embodiment, the subject suffers from ataxia. Preferably, the subject suffers from spinocerebellar ataxia.

In an embodiment, the processor outputs the stimulation signal to the neural electrode continuously until the processor determines that the abnormal motor movement no longer exists.

In another aspect, the present invention pertains to a method of modulating an abnormal motor movement of a subject by using a neurostimulation system, the method comprising:
implanting a EMG electrode in the subject, wherein the EMG electrode is in communication with a data acquisition unit which receives and transmits a EMG signal;
implanting a neural electrode in a deep cerebellar nuclei of the subject;
processing the EMG signal via a processor to generate a EMG pattern based on the EMG signal, and outputting a stimulation signal to the neural electrode when the EMG pattern is indicative of the abnormal locomotion.

In an embodiment, more than one EMG electrode is implanted in tibialis anterior and/or gastrocnemius muscle.

In an embodiment, the subject suffers from ataxia. Preferably, the subject suffers from spinocerebellar ataxia.

In an embodiment, the processor includes a field-programmable gate array.

In an embodiment, the data acquisition unit is in communication with the neural electrode for recording neuronal activity of the subject during a gait movement.

In an embodiment, the processor generates a gait cycle based on the EMG pattern and optionally neuronal activity recorded by the neural electrode.

In an embodiment, the processor compares the gait cycle with pre-set gait cycle data to determine whether the EMG pattern is indicative of the abnormal motor movement.

In an embodiment, the data acquisition unit communicates with the processor via a wireless network.

In an embodiment, the processor outputs the stimulation signal to the neural electrode via a stimulus generator.

In an embodiment, the processor outputs the stimulation signal to the neural electrode continuously until the processor determines that the abnormal motor movement no longer exists.

The neurostimulation system and method of the present invention are particularly useful in modulating a motor movement particularly a locomotion of a subject such as a patient who is suffering from ataxia. The deep brain stimulation at the deep cerebellar nuclei helps the subject to improve his/her motor movement and minimize the risk of getting injured as a result of ataxia. The present invention may also be useful in rehabilitation and other medical purposes.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 5A shows the processed EMG patterns and DCN neuronal pattern of the control group after synchronization of the EMG pattern with DCN neurospike and local field potential.

DETAILED DESCRIPTION OF THE INVENTION

Figure 1:
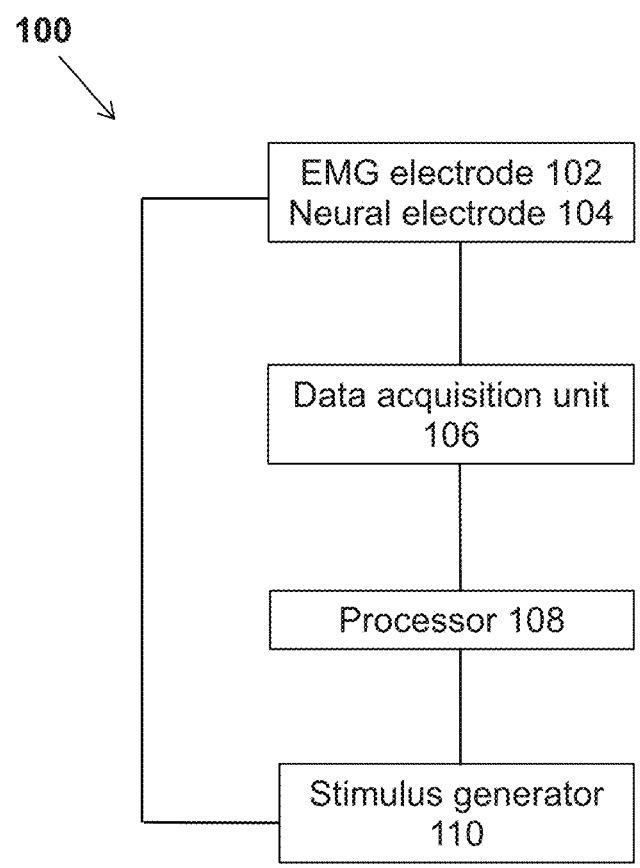
FIG. 1 is a schematic diagram showing a neurostimulation system of an embodiment of the present invention.

Unless otherwise defined, all technical terms used herein have the same meaning as commonly understood by one skilled in the art to which the invention belongs.

As used herein, the forms "a", "an", and "the" are intended to include the singular and plural forms unless the context clearly indicates otherwise.

The present invention in a first aspect provides a neurostimulation system for modulating abnormal motor behaviour, i.e. abnormal motor movement, of a subject. The neurostimulation system includes
an electromyographic (EMG) electrode;
a neural electrode implantable in a deep cerebellar nuclei of a subject;
a data acquisition unit in communication with the EMG electrode for receiving and transmitting a EMG signal; and
a processor in communication with the data acquisition unit, the processor generates a EMG pattern based on the EMG signal and outputs a stimulation signal to the neural electrode when the EMG pattern is indicative of an abnormal motor movement.

The term "subject" of the present invention in particular refers to an animal or human, in particular a mammal and most preferably a human being. The subject who is particularly benefit from the present invention is an individual who has abnormal motor movement compared to ordinary healthy individuals.

In an embodiment, the subject suffers from ataxia. The ataxia may be associated with a neurodegenerative disease such as, but not limited to, spinocerebellar ataxia (SCA), Parkinson's disease, essential tremor, and epilepsy. In a particular embodiment, the subject suffers from spinocerebellar ataxia (SCA). SCA is a neurodegenerative disease characterized by loss of body balance and motor coordination, speech and oculomotor difficulties. The neurostimulation system of the present invention applies deep brain stimulation (DBS) technology to modulate the abnormal motor movement of the subject. The neurostimulation system herein is capable of stimulating deep cerebellar nuclei of the subject for modulating SCA-associated motor symptoms, e.g. symptomatic locomotion, thereby alleviating the symptoms.

The stimulation at the deep cerebellar nuclei (DCN) is exceptionally suitable for the present invention as DCN is the major motor command centre. The major output is from Purkinje cells projecting to the DCN. DCN acts as a relay center to receive inputs from Purkinje cells in the cerebellar cortex and projects to various pre-motor areas for fine tuning of motor activity. Therefore, the neural electrode is preferably implanted in the DCN to achieve the desired modulating effect of the present invention.

"Modulating" the abnormal motor movement includes inhibiting symptomatic locomotion, improving gait speed, improving postural stability, inhibiting tremor, and the like. It would be appreciated that the modulation may be resulted from changes of the neuronal activities such as, but not limited to, an increase in interspike interval and a decrease in neuronal firing after deep brain stimulation. Suitable devices and methods can be used to determine the modulating effect of the deep brain stimulation of the present invention.

FIG. 1 illustrates a schematic diagram of the neurostimulation system of an embodiment of the present invention. The neurostimulation system 100 includes an EMG electrode 102 for retrieving EMG signals of a subject during movement. The EMG electrode 102 may be configured as a surface EMG electrode or an intramuscular EMG electrode. In an embodiment, the EMG electrode is provided to detect and record EMG signals generated in muscles during a gait movement of the subject. The gait is preferably referred to a natural gait such as, but not limited to, walking, jogging, running, and sprinting.

In an embodiment, the neurostimulation system 100 includes one or more EMG electrodes 102, for example at least 2 or at least 4 electrodes, to be implanted in the subject's muscle particularly muscle of a limb. For example, the EMG electrodes 102 may be implanted in one or more muscles selected from the group consisting of tibialis anterior, gastrocnemius muscle, rectus femoris, biceps femoris, biceps brachii, vastus lateralis, and combinations thereof.

The EMG electrode 102 is in communication with the data acquisition unit 106 which receives and records the EMG signal transmitted from the EMG electrode 102. The data acquisition unit 106 may be an electronic device such as a computer or a portable device that is equipped with data acquisition software to collect EMG signals from the EMG electrode 102 and forward them to the processor 108 for further processing. The data acquisition unit 106 may be connected to the EMG electrodes via a wired or wireless network.

In an embodiment, the data acquisition unit 106 is provided by way of a portable device or a small sized electronic device which can be carried by or attached on the subject. The data acquisition unit 106 communicates with the EMG electrode 102 via a wireless network or a wired network.

The neurostimulation system 100 includes a processor 108 for processing the EMG signal transmitted by the data acquisition unit 106. The processor processes and analyses the EMG signal to generate a EMG pattern based on the EMG signal. The processor 108 may further include a controller. In an embodiment, the processor 108 may be a microcontroller. Preferably, the processor 108 includes a programmable logic unit selected from a field-programmable gate array (FPGA) or an application-specific integrated circuit (ASIC). The FPGA is capable of processing real-time data at a high computational speed, e.g. completing one second real world activity within milliseconds. This is advantageous in that it can detect real-time abnormal motor movement particularly abnormal locomotion and respond to the abnormal motor movement in a short period of time or almost instantaneously.

In an alternative embodiment, the processor 108 is a PC/104 based computer system, optionally a micro-sized PC/104 based computer system, with built-in connectors.

The processor 108 may communicate with the data acquisition unit 106 via a wired or wireless network. It would be understood that the processor 108 may be configured in various shapes or incorporated with another device. The processor 108 may be implanted in the subject, attached on the subject or carried by the subject depending on the configuration of the processor 108 and the arrangement of the neurostimulation system 100. In an embodiment, the processor 108 is attached on the subject. In another embodiment, the processor 108 may be a portable device carried by the subject.

In the present invention, the processor 108 determines whether the EMG pattern is indicative of an abnormal motor movement. In particular, the processor 108 compares the EMG pattern with a set of pre-set data. The processor 108 may generate a gait cycle based on the EMG pattern and optionally neuronal activity detected by the neural electrode 104, and then compare the gait cycle with the pre-set gait data stored in the processor 102. The pre-set gait data is preferably derived based on healthy individuals who have the same age and sex as the subject. When the processor 108 determines there is an abnormal motor movement, e.g. an increase in the swing or stance phase, an increase in mean neuronal firing rate, an increase in number of bursts, and/or a decrease in interspike interval compared to the pre-set data, then the processor 108 outputs a stimulation signal to the stimulus generator 110 so as to deliver a pulse to deep cerebellar nuclei through the neural electrode 104. The deep cerebellar nuclei will be stimulated and the motor movement of the subject will then be modulated.

The processor 108 may include one or more algorithms to analyze the EMG signals, and/or filter noise. In an embodiment, the EMG signals are subject to rectification, median filter, and/or root mean square amplitude for optimization.

The determination of whether the subject is having abnormal motor movement is a real-time process. In other words, the neurostimulation system 100 can monitor the movement of the subject for a long period of time, for example for more than 5 hours, more than 10 hours or more than 15 hours, and output a stimulation signal to the neural electrode 104 within a relatively short period of time or almost instantaneously when the abnormal motor movement is detected. Accordingly, the present invention can provide a quick solution to monitor and modify the abnormal motor behavior of the subject.

In an embodiment, the processor 108 outputs the stimulation signal to the neural electrode 104 continuously until the processor determines that the abnormal motor movement no longer exists. The neurostimulation system 100 is thus useful to minimize side effects caused by excessive continuous stimulations. In an alternative embodiment, when the processor 108 detects that the subject is having a certain motor movement which may be highly associated with ataxia, the processor 108 may automatically send the stimulation signal corresponding to said motor movement before determination of any abnormal behaviour so as to ensure the subject can move in a proper manner.

The processor 108 may be in wired or wireless communication with the neural electrode 104 and the stimulus generator 110. The neural electrode 104, as discussed above, is preferably implanted in a DCN. The DCN includes dentate nucleus, emboliform nucleus, globose nucleus, and fastigii nucleus. The neural electrode 104 may be implanted to stimulate at least two or more of the dentate nucleus, emboliform nucleus, globose nucleus, and fastigii nucleus.

The neural electrode 104 may be in communication with the data acquisition unit 106 so that the data acquisition unit 106 can record the neuronal activity of the subject during a gait movement. The neuronal activity may be useful in the generation of the EMG-based gait cycle. The EMG pattern may be synchronized with the neuronal activity such as firing pattern to better define the gait cycle.

It would be appreciated that the neurostimulation system may include further electrodes such as reference electrodes and grounding electrodes during implementation, as well as connectors and batteries for establishing a complete circuit. A person skilled in the art would appreciate suitable circuits for the present invention.

In another aspect, the present invention pertains to a method of using the neurostimulation system of the present invention to modulate the abnormal motor movement of a subject. The method includes the use of the neurostimulation system as described above, and the subject is also as defined above. In particular, the method includes the steps of:
  implanting a EMG electrode in the subject, wherein the EMG electrode is in communication with a data acquisition unit which receives and transmits a EMG signal;
  implanting a neural electrode in a DCN of the subject preferably human;
  processing the EMG signal via a processor to generate a EMG pattern based on the EMG signal, and outputting a stimulation signal to the neural electrode when the EMG pattern is indicative of the abnormal motor movement.

Preferably, there may be more than one EMG electrode. Preferably, the more than one EMG electrode is implanted in tibialis anterior and/or gastrocnemius muscle.

It would be appreciated that the neurostimulation system and method of the present invention are useful to modulate the abnormal motor behaviour of a patient who is suffering from a neurodegenerative disease, particularly a cerebellar disorder. The present invention can be applied in medical applications such as for treating motor disorders associated with neurodegenerative diseases, rehabilitation activities, and the like.

EXAMPLES

Animal Model of Spinocerebellar Ataxia (SCA)

The inventors used Lhx1/5 double knockout mice (denoted as DKO mice) as a model of SCA. DKO mice possess ataxia phenotypes, for example decreased cerebellum size due to reduction of dendritic length, branching of the mutant Purkinje cells (PCs) and increased interneuron density leading to decreased molecular layer. Noticeable ataxic motor movement was observed at about 3 weeks after birth and tremor became prominent while walking on narrow beam platform of low diameter.

The inventors tested the motor coordination of the DKO mice by using rotarod test and DKO mice showed significantly decreased retention time on rotarod spindle (<10 seconds) as compared to controls. Therefore, spinocerebellar ataxia like symptoms appears in DKO due to dysfunction of input and output pathways.

All experiments were followed as per the guideline of Government of Hong Kong (SAR), Department of Health. Adult male Lhx1/5 DKO and control mice (8-10 weeks old) were used. Neurobehavioral assessment for motor coordination deficit was evaluated by rotarod test, pole climb test, beam walking test, walking track analysis test and videokinematics, electrophysiological test (gastrocnemius EMG) before and after DCN stimulation.

Preparation and Implantation of Electrodes in Mice

Figure 2A:
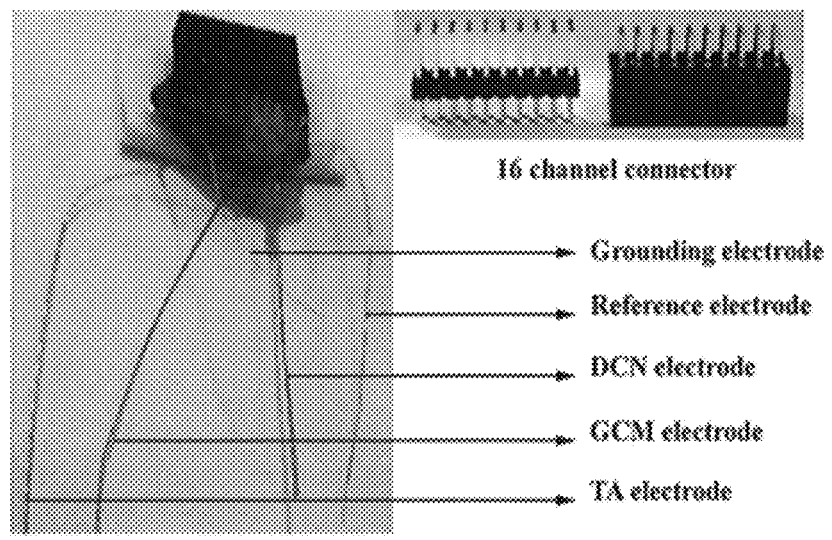
FIG. 2A is a picture showing an arrangement of a connector connecting to a neural electrode, EMG electrodes including GCM electrodes and TA electrodes, a reference electrode, and a grounding electrode.

As shown in FIG. 2A, a 20 pin connector was customized to configure the arrangement of the neural electrode and EMG electrode simultaneously using stainless steel and nichrome wire. Four electrodes were used as the neural electrodes and another four electrodes were used as EMG electrodes. Among the EMG electrodes, two were arranged to be implanted in gastrocnemius muscle and two were arranged to be implanted in tibialis anterior muscle. The remaining channels were grounded with grounding site (right corner pin) and reference electrode was configured on the left corner. Silver conductive paint was used to increase the conductance and the whole assembly was covered with epoxy glue.

After the fabrication, electrodes were tested using the oscilloscope and stimulus isolator to check the flow of current and connection.

Figure 2B:
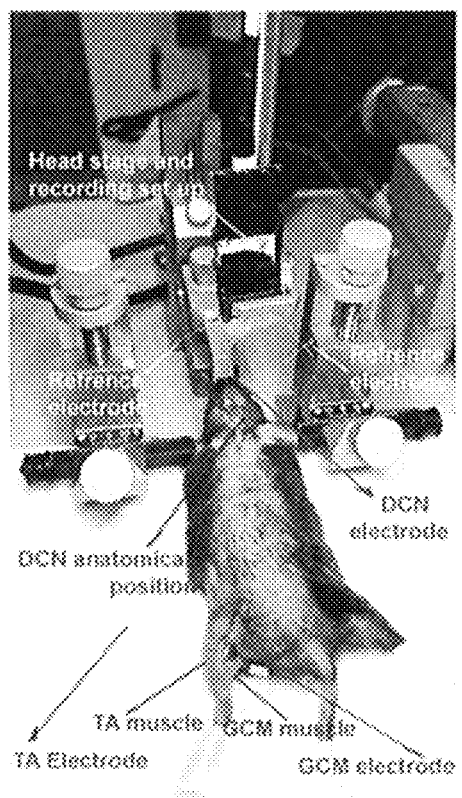
FIG. 2B shows the set-up of implantation and fixation of the electrodes on a mouse.

Referring to FIG. 2B, there is shown the set-up for implantation of electrodes.

Implantation of Neural Electrodes at Deep Cerebellar Nuclei

Mice were anesthetized with ketamine (100 mg/kg) and Xylazine (10 mg/kg) and placed in the stereotactic frame. Buprenorphine (75 µg/kg) was administered before surgery and the morning following surgery to relieve pain. A midline skin incision (10 mm) was made to locate the bregma and lambda sutures for precise stereotaxic electrode placement. The neural electrodes were bilaterally within the radius of 0.5 mm around the central point relative to the bregma (−6.4 mm anteroposterior, +1.3 mm lateral and 2.5-3 mm deep) into the deep cerebellar nuclei and fixed to the skull with dental cement.

Implantation of EMG Electrodes in Tibialis Anterior and Gastrocnemius Muscles

After implantation of neural electrodes, a 1-cm incision was made on the back over the lumbar spine. The skin was separated from the underlying fascia and the bundle of wires tunneled subcutaneously from the back to each leg incision. The skin was pulled tight and the connector was secured on the head with dental cement. Electrodes wires were attached with a needle (27"½ gauge), pierced perpendicular to the muscle fibbers until the stripped region of the electrode was within the muscle tissue. Two electrodes were placed at a distance of approximately 1 mm. Extra wire were looped and pushed underneath the skin and sutured. Antibiotic and analgesic (Meloxicam, 1 mg/ml, i.p; Buprenorphine, 75 µg/kg, i.m) were administered before surgery, the morning following surgery and observed till full recovery. Mice were housed alone with minimal firm obstructions within the cage in order to protect the connector. Spontaneous EMG were recorded from gastrocnemius muscle (Bio-signal Technologies Inc., USA) and data were analyzed on FPGA board using customized programmes and offline analysis was performed by Spike 2 (Tysseling et al., 2013, Au et al., 2016).

Analysis of EMG Signals

As described above, four EMG electrodes were implanted in the tibialis anterior and gastrocnemius muscles of the mice. Reference and grounding electrodes for EMG were fixed on the skull. After recovery, the mice were allowed to move freely and the EMG signals produced during the movement were recorded. The recorded file was opened in SPIKE 2 software and processed using the function of channel process. Data was rectified, smoothened. A median filter and root mean square (RMS) amplitude function were also applied. The inventors then first optimized EMG of gastrocnemius (GCM) and tibialis anterior (TA) muscle to define the phase of gait cycle based on the EMG activity, particularly the swing and stance phase. The stance time was also calculated.

Figure 3A:
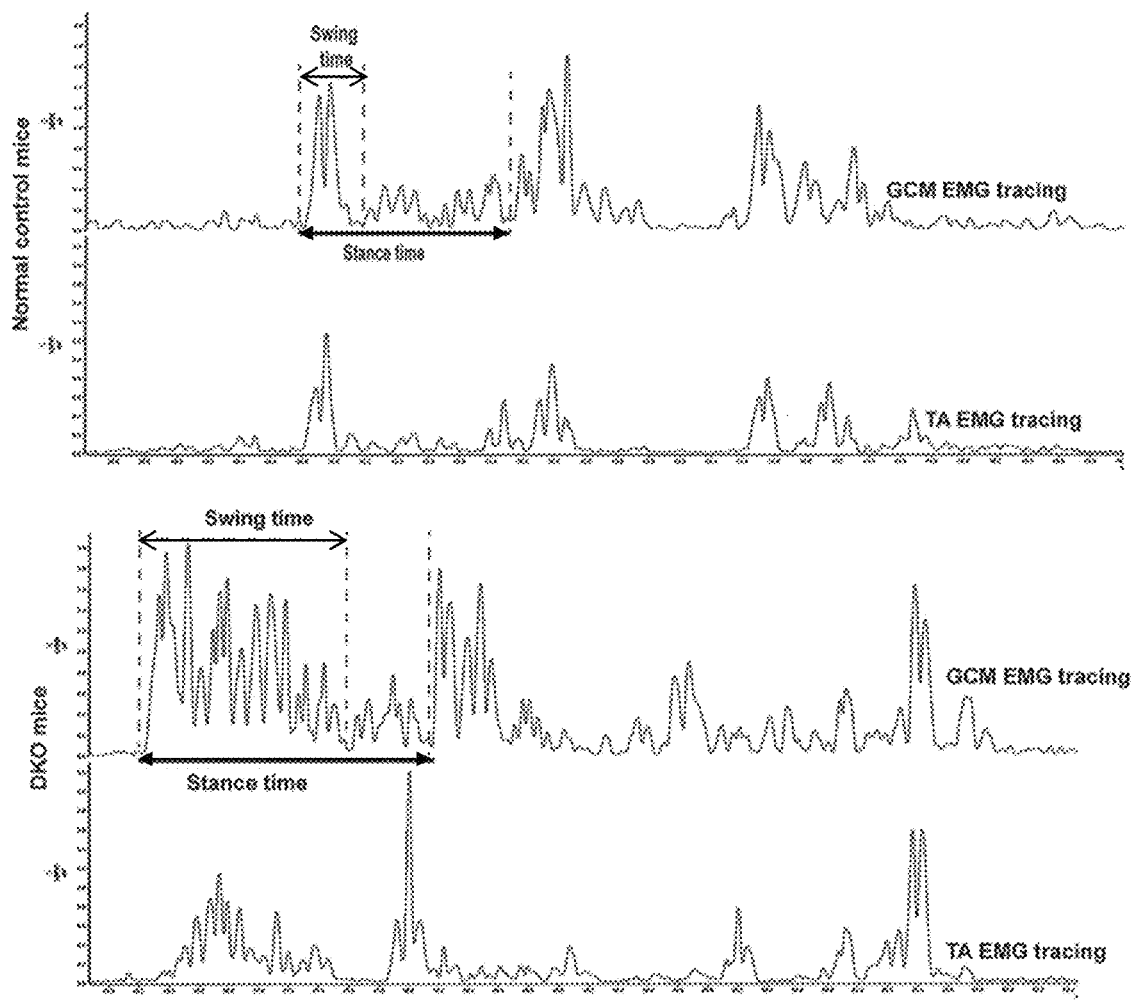
FIG. 3A shows a EMG pattern of the control group (normal mice) and an EMG pattern of the DKO group (DKO mice) with stance and swing time indicated.

Referring to FIG. 3A, the period of stance time and swing time are identified and indicated in the plots. It is observed that mice in the control group showed steady pace with sharp peak of EMG and normal range of stance time. In contrast, the DKO mice showed unstable walking, early onset of muscle activities in stance phase, significantly increased stance and swing time, variation in EMG amplitude, and their abnormal activities from stance-to-stance phase and stance-to-swing phase. These results together suggest that the DKO mice have abnormal limb flexion.

Figure 3B:
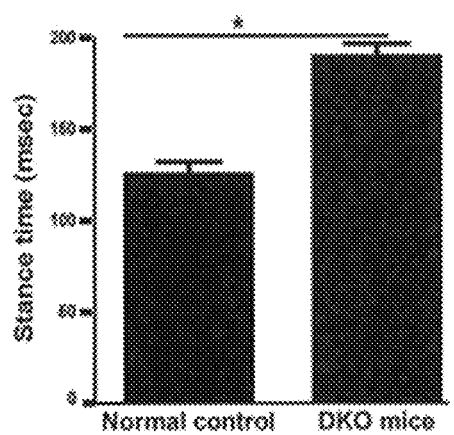
FIG. 3B is a plot showing the stance time of the control group and the DKO group, in which DKO group had a longer stance time compared to the control group.

Further, the stance time was calculated and FIG. 3B shows the stance time of mice in control group and DKO group. DKO mice have a remarkably longer stance time as compared to the control group. Values represented mean±SEM (n=5-7). *$P<0.05$, Student's t-test.

Analysis of Neuronal Data

The inventors further determined the electrophysiological properties of deep cerebellar nuclei neurons during motor movement period of the mice. After recovering from the implantation, recording connector of acquisition system was attached with electrode connector fixed on the mice's head using mild isoflurane anesthesia. Mice were acclimatized in the cage with wire for 15 minutes and recording was performed. Time was recorded for step-up and step-down time to find the changes occurring during the walking of the mice.

Figure 4A:
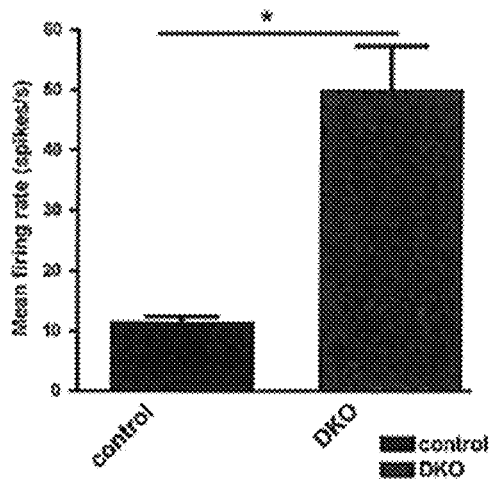
FIG. 4A is plot of mean firing rate of the control group and DKO group.
Figure 4B:
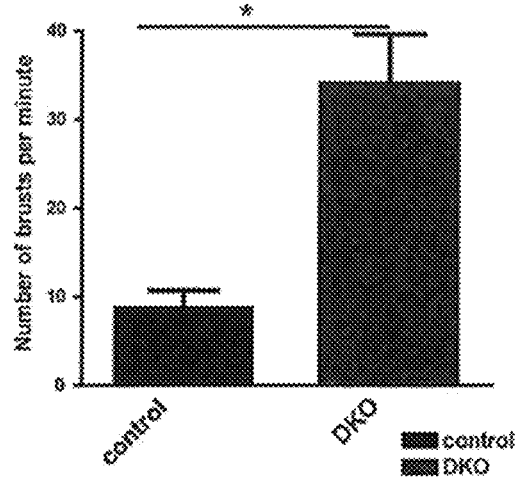
FIG. 4B is a plot of number of bursts of the control group and DKO group.
Figure 4C:
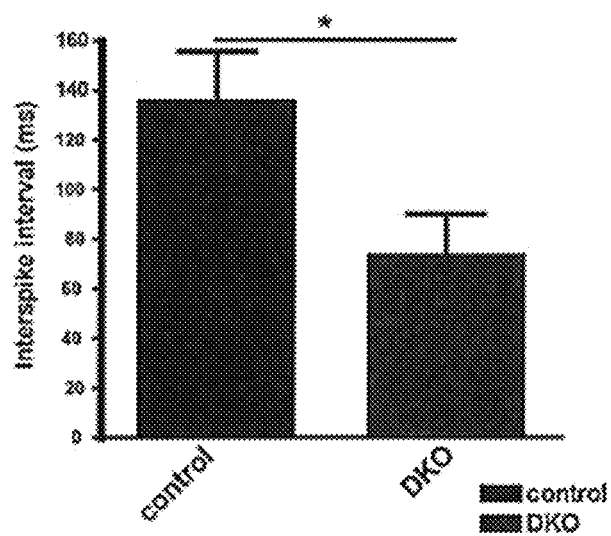
FIG. 4C is a plot of interspike interval of the control group and DKO group.

As shown in FIG. 4A to FIG. 4C, DKO mice showed a significant increase in mean firing rate, an increase in number of bursts per minute, and a decrease in inter spike interval.

Figure 4D:
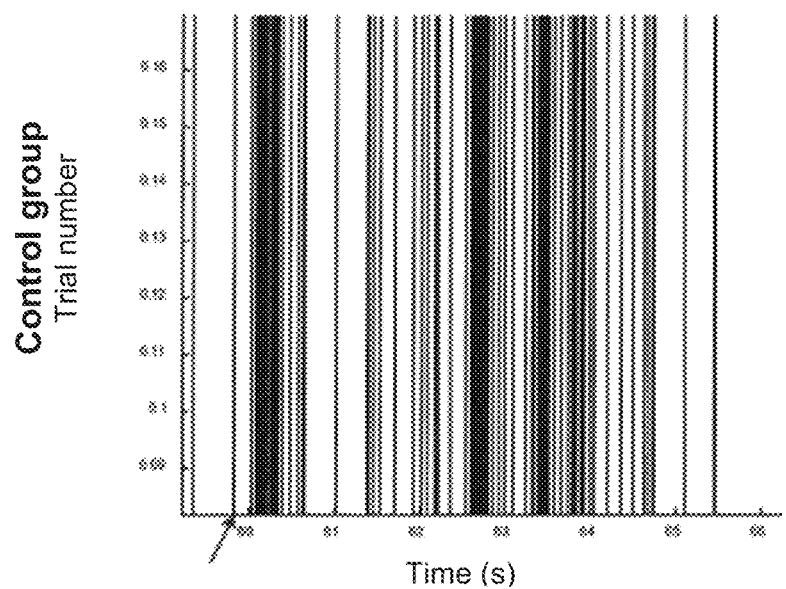
FIG. 4D is a DCN neuronal firing pattern of the control group.
Figure 4E:
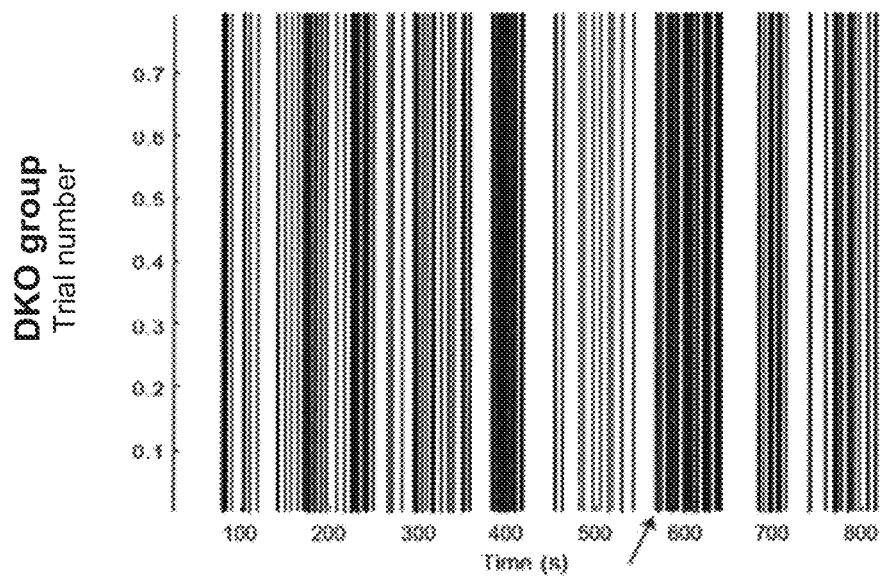
FIG. 4E is a DCN neuronal firing pattern of the DKO group.
Figure 4F:
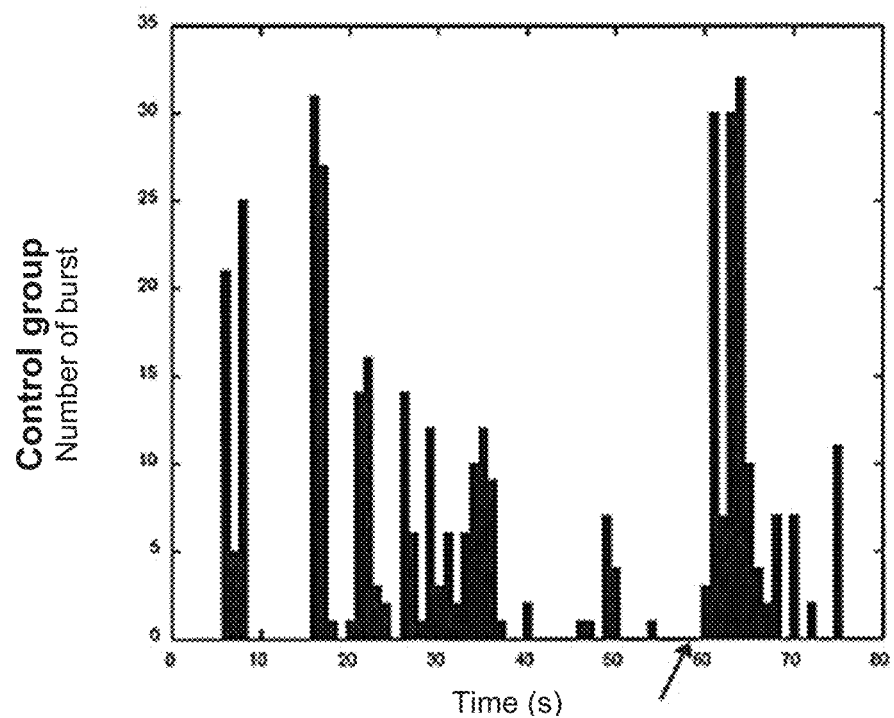
FIG. 4F is a plot of absolute number of bursts with time in the control group.
Figure 4G:
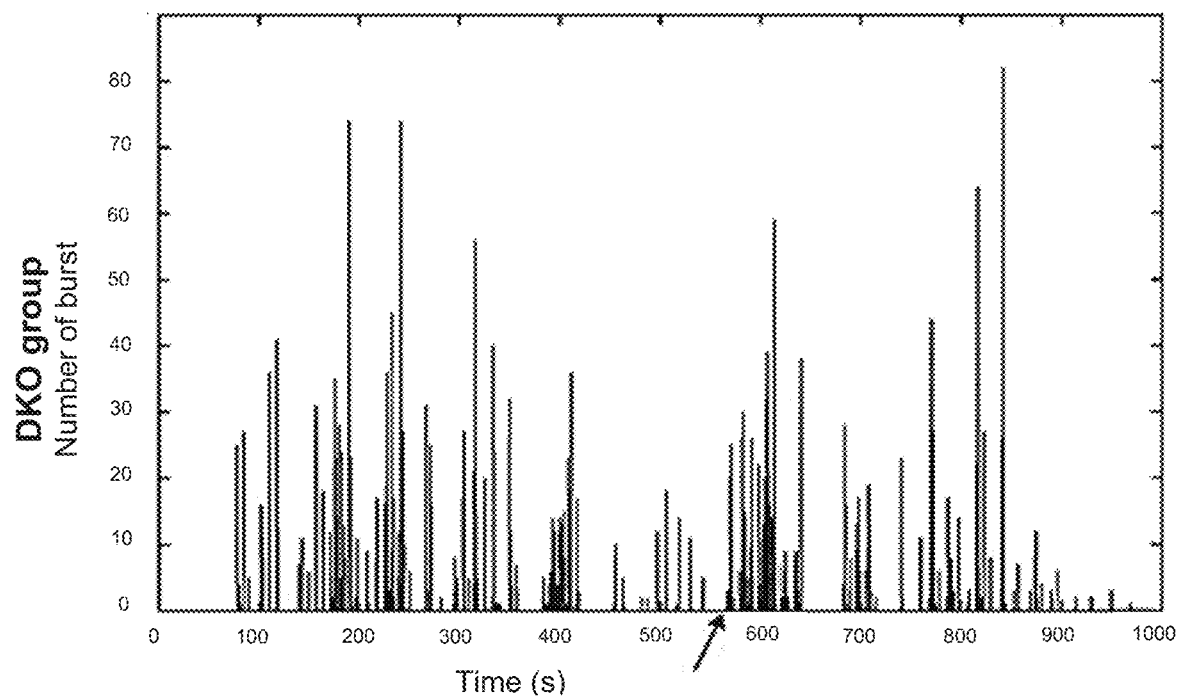
FIG. 4G is a plot of absolute number of bursts with time in the DKO group.

Tracing of DCN neuronal firing in the control group and DKO group are shown in FIG. 4D and FIG. 4E. The arrow represents the initiation of step-up time. Furthermore, the absolute number of bursts with time in the control group and DKO group is shown in FIG. 4F and FIG. 4G respectively. DKO mice showed an increase in the number of bursts. The initiation of step-up time point was indicated by the arrow. Values represented mean±SEM (n=5-7). *P<0.05, Student's t-test.

Synchronization of the EMG and Neuronal Data

Different filters were used for recording the EMG signals and neuronal signals to optimize the signals and remove background noise. In particular, the filter was optimized first along with the sampling rate. For EMG signals, the recorded file was processed using the function of channel process. Background noise of the data was removed using DC remove in channel process. Further, data was rectified and smoothened. A median filter was applied and root mean square (RMS) amplitude was determined. For DCN neurospike, neurospike was recorded using low pass and high pass filter and customized MATLAB program was used for the conversion of file and analysis. For local field potential (LFP), same neurospike channel was split in two copies so the inventors could record the neurospike and LFP of same neuron synchronized with time.

Figure 5B:
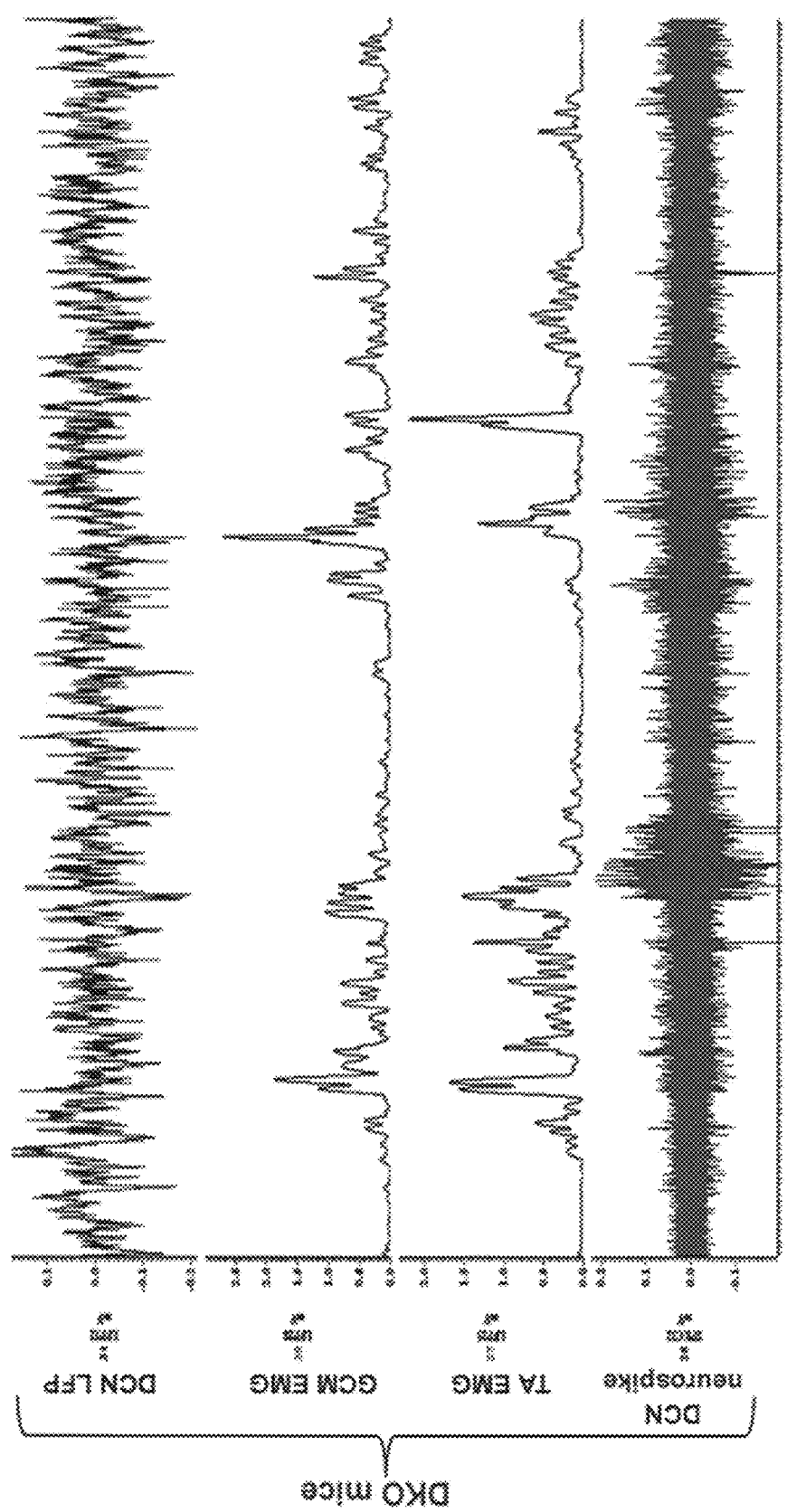
FIG. 5B shows the processed EMG patterns and DCN neuronal pattern of the DKO group after synchronization of the EMG pattern with DCN neurospike and local field potential.

Referring to FIGS. 5A and 5B, raw traces of synchronized EMG with DCN and LFP recording showed DKO mice had rapid increase in the neuronal firing and total power of LFP synchronously with the peak of the EMG as compared with the control group (n=5-7).

Synchronization of EMG with Video Kinematics

Mice were trained for 3 days (5 sessions per day) to walk on a walking track (100 cm length, 3 cm width and 10 cm height). Mice were anesthetized with isoflourance and IR-reflective microdots were attached at metatarsophalangeal joint, ankle joint, knee joint, hip joint, and iliac crest with tissue glue. Recording head stage connector was plugged into socket of the electrodes. After recovery from anaesthesia, mice were allowed to acclimatize with reflector and head stage for 15 minutes and trained to walk spontaneously at constant speed. A high-speed camera (500 frames per second) was used for video recording after adjusting the distance of camera to reflector, aperture and contrast to minimize the background. Stride length and stance time were analysed by MaxTraQ (Innovision system Inc., USA).

Figure 6A:
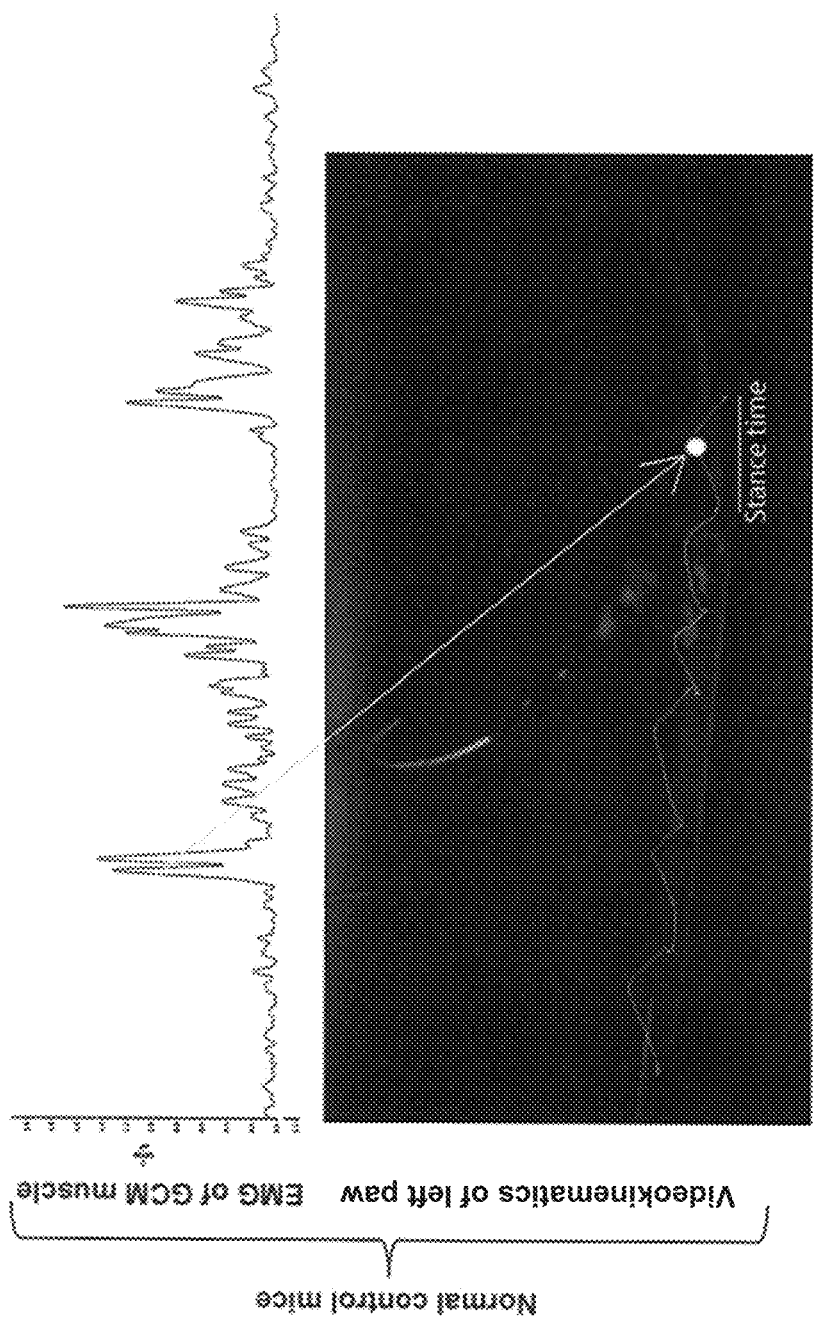
FIG. 6A shows the videokinematic tracing results of the control group with reference to EMG pattern.
Figure 6B:
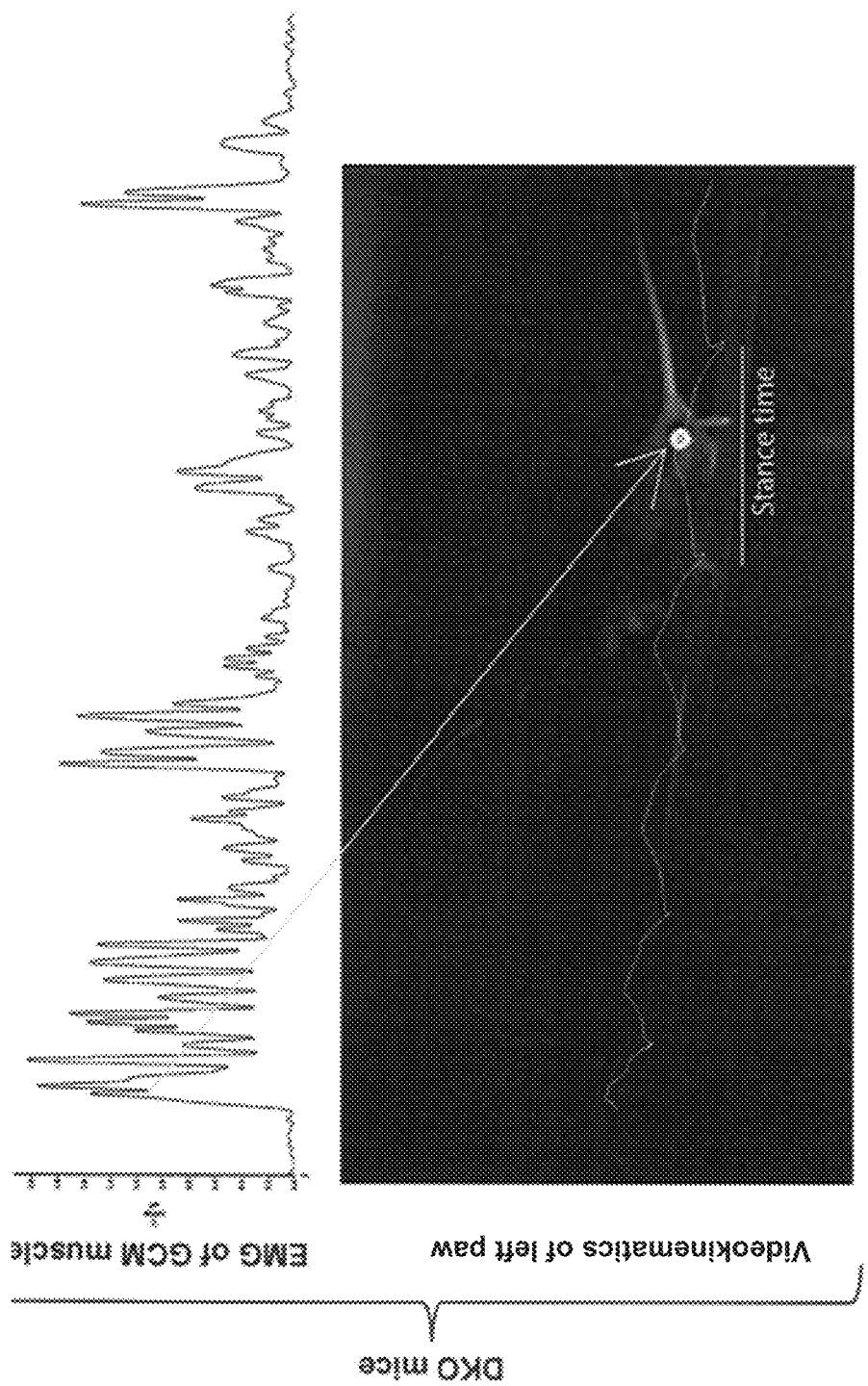
FIG. 6B shows the videokinematic tracing results of the DKO group with reference to EMG pattern.

Video was digitized and track was plotted automatically using MaxTraQ software (Innovision system Inc., USA). Raw traces of walking pattern as well as video were saved for future analysis. EMG data recording were synchronized manually with video kinematics recording for finding the pattern of gait cycle with EMG. Same time frame was selected to correlate the EMG activity peak with the tracing of the video kinematics. The arrows in FIGS. 6A and 6B indicate the swing phase of the EMG with video kinematics. The control group shows a normal range of stance and swing time, while the DKO group shows an ataxic gait by increased variation of stance and swing times, exaggerated hind limb flexion and significant increase in the stance time compared to the control group (n=5-7).

Deep Cerebellar Nuclei Electrode Stimulation

EMG signal from the mice was recorded by the data acquisition system. In this example, the signal was streamed over UDP at 1000 Hz to the processor and controller FPGA board. The FPGA board analyses the EMG signal to differentiate normal and symptomatic EMG pattern. Once a symptomatic pattern is detected, a stimulation signal, particularly a stimulation pulse train will be output from the FPGA and delivered as a DBS to the DCN through the neural electrodes implanted on the mice.

The neural electrodes implanted in DCN were configured to be simulated by iso-flex stimulus isolator (AMPI, Israel) and 9 channel stimulus generator (Master 9, AMPI, Israel). All stimulations were set at a pulse width of 60 µs, pulse amplitude of 100 µA, frequency of 130 Hz for 1 h in an open-loop deep brain stimulation (DBS). For a closed-loop DBS, stimulation was set at 100 µA current and 60 µs pulse width.

Neurobehavioral Tests on the Mice

To determine whether the neurostimulation system of the present invention is useful in modulating an abnormal motor behaviour of the mice, several tests were conducted by using the control group and DKO group. The tests are pole climb test, walking track analysis, rotarod test, and narrow beam walk test.

After implantation of the electrodes, mice were allowed to recover for a week and then subjected to the tests.

Pole climb test was use to assess motor dysfunction. Mice were placed on the top of a 100-cm vertical pole (diameter of 1 cm). Video tracking system (ANY-maze, Stoelting, USA) was used to track the mice and calculate the descent latency by automated software. Recording was started when the mice began the turning movement and total time to descend to the floor was recorded. The test was repeated 3 times and the average descent time was used for data analysis.

For walking track test, mice were habituated for 3 sessions over 5 days and allowed to walk in a narrow corridor covered with white paper strip (10×60 cm). The hind paws of the mice were painted red and fore paws were painted blue and the mice were allowed to walk on the white paper strip. Footprints were taken from each animal before and after treatment. Three parameters were calculated for evaluation of (1) stride length: distances between consecutive positions occupied by the right hind paw (2) Sway length: between the positions of the two front paws and (3) stance length: between the positions of the two hind paws (Girirajan et al., 2008).

For the rotarod test, motor coordination was evaluated using rotarod apparatus (LE8500, BIOSEB, France). Mice were trained for 3 sessions over 5 days at initial speed of 4 rpm and then progressively increased to accelerated mode for 2 min. Mice that stayed on the rotarod spindle for at least 60 s were selected for the experiment. Baseline of the rotarod test was performed at an accelerated mode (4-40 rpm) for 5 min and the mean latency to fall off (retention time on rotarod spindle) was used for evaluation purposes. Animals were given minimum 15 min to rest between each trial (Au et al., 2016).

The beam walk test assesses fine motor coordination and balance. Mice were trained to cross a wooden round beam, 100 cm long, 1 cm diameter, and 50 cm above the bench. Time to traverse the beam was determined using ANY-maze video tracking system (ANY-maze, Stoelting, USA).

According to the results, as shown in FIG. 7 to FIG. 10, DKO mice showed a statistically significant increase in descent latency in the pole climb test, a decrease in stride length in the walking track test, a decrease in retention time on the rotarod spindle and an increase in transverse latency in the narrow beam walking test, as compared with the control group ($p<0.05$). Accordingly, the mice in the DKO group were confirmed to have a motor deficit.

After confirmation of the locomotion of the DKO group mice, the mice were subject to continuous DCN stimulation to determine whether the DCN stimulation can help to modulate the abnormal motor behaviour. The DCN stimulation was conducted as described above. In particular, mice were lightly anesthetized with isoflurane and connecting wire was attached with electrode connector. Mice were allowed to acclimatize in the cage with wire for 15 minutes. DCN was simulated at 100 µA current, 60 µs pulse width, at a frequency of 130 Hz continuously for 1 h.

Figure 7:
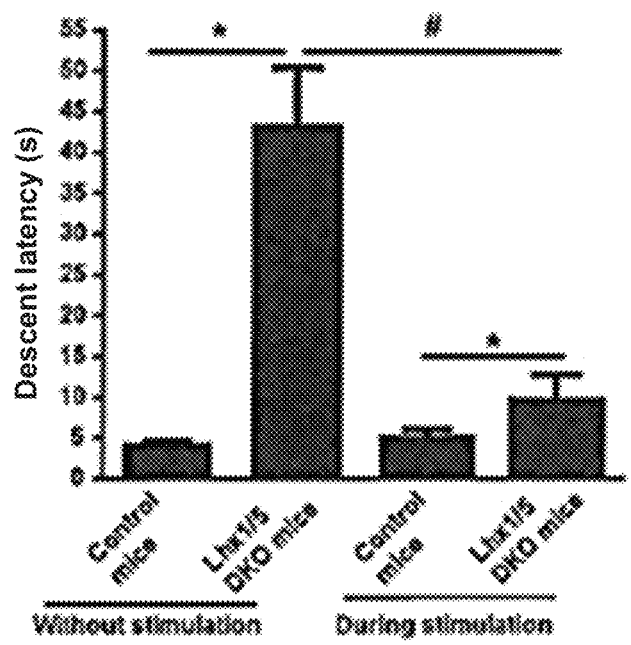
FIG. 7 is a plot of descent latency of the control group and the DKO group before and after DCN stimulation, determined under the pole climb test.
Figure 8:
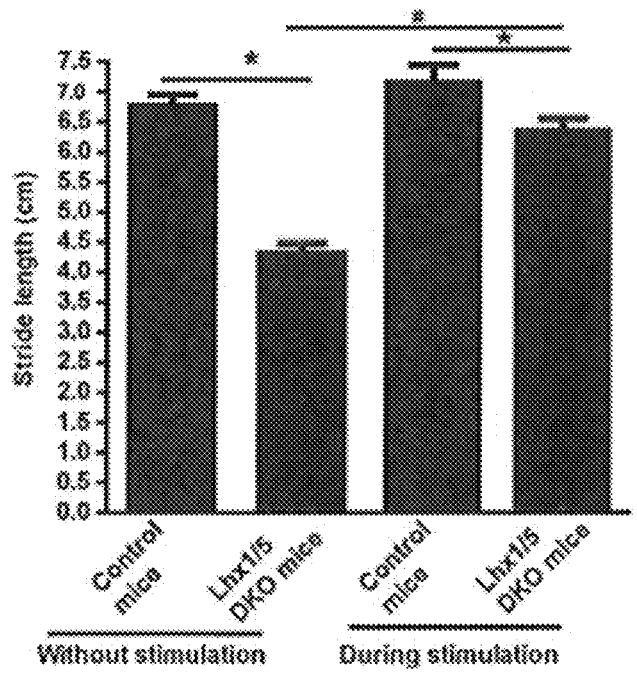
FIG. 8 is a plot of stride length of the control group and the DKO group before and after DCN stimulation, determined under the walking track test.
Figure 9:
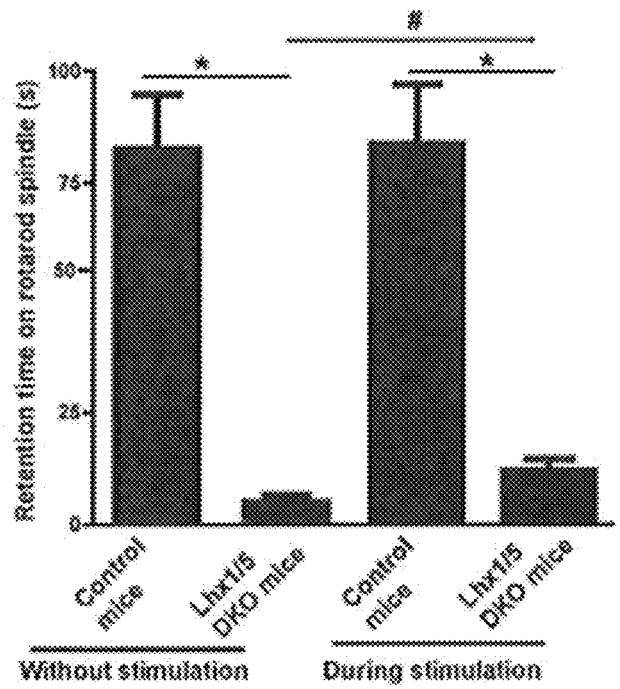
FIG. 9 is a plot of retention time of the control group and the DKO group before and after DCN stimulation, determined in the rotarod test.
Figure 10:
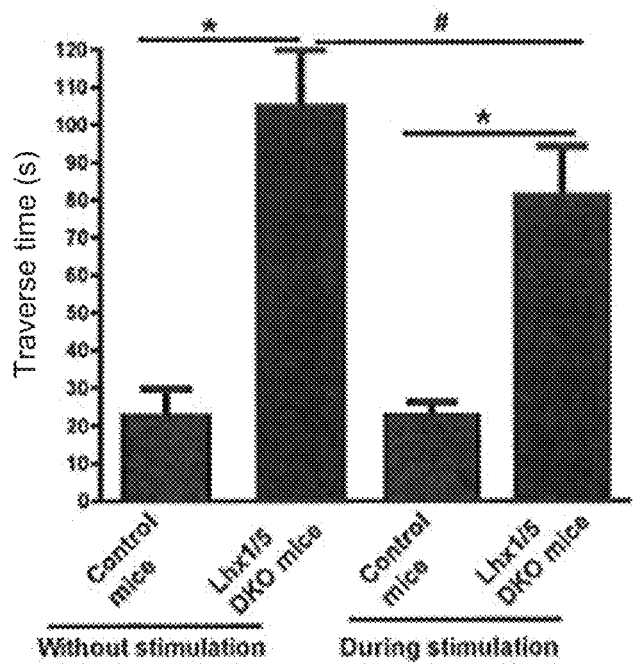
FIG. 10 is a plot of transverse time of the control group and the DKO group before and after DCN stimulation, determined in the narrow beam walking test.

Mice in the DKO group and control group were subject to the neurobehavioral tests as described above during the DCN stimulation. The mice in the control group did not show significant change during the DCN simulation. Referring to FIG. 7, when the DKO group mice were subject to DCN stimulation, the mice have decreased descent latency in the pole climb test, as compared to DKO mice without DCN stimulation. FIG. 8 shows that the DKO mice receiving DCN stimulation have an increased stride length in the walking track test, as compared to DKO mice without DCN stimulation. FIG. 9 and FIG. 10 show that the DKO mice receiving DCN stimulation have a slightly longer retention time on a rotarod spindle and decreased transverse latency in the narrow beam walking test, as compared to DKO mice without DCN stimulation. All data are presented as mean±SEM, * $P<0.05$ (n=5-7) as compared with the control group, # as compared with the DKO mice without stimulation.

Based on the results, it is thus shown that the neurostimulation system of the present invention is useful and effective in modulating abnormal motor behaviour of a subject. The stimulation at DCN advantageously improves the motor activity of the subject, allowing the subject to move or walk faster and in a more stable manner. Accordingly, the neurostimulation system and the method of the present invention can be applied in medical applications such as for treating motor disorders associated with neurodegenerative diseases, rehabilitation activities, and the like.

The invention claimed is:

1. A neurostimulation system for modulating abnormal motor movement of a subject suffering from spinocerebellar ataxia, comprising
   an electromyographic (EMG) electrode for detecting an EMG signal generated in a muscle of a subject during a gait movement of the subject;
   a neural electrode arranged to be implanted in a deep cerebellar nuclei of the subject for detecting neuronal activity of the subject during the gait movement of the subject and for providing a stimulation signal to the deep cerebellar nuclei;
   a data acquisition unit in communication with the EMG electrode for receiving and transmitting the EMG signal; and
   a processor in communication with the data acquisition unit and the neural electrode, the processor:
      generating an EMG pattern based on the EMG signal detected by the EMG electrode;
      synchronizing the EMG pattern with the neuronal activity detected by the neural electrode;
      generating a gait cycle based on the synchronized EMG pattern and neuronal activity;
      comparing the gait cycle with pre-set gait cycle data to determine the presence of abnormal motor movement associated with spinocerebellar ataxia in the subject; and
      upon determining presence of the abnormal motor movement, outputting a stimulation signal to the neural electrode to deliver a pulse to the deep cerebellar nuclei of the subject, thereby modulating the abnormal motor movement associated with spinocerebellar ataxia in the subject;
   wherein the neurostimulation system is a closed-loop neurostimulation system.

2. The neurostimulation system of claim 1, wherein the processor includes a field-programmable gate array.

3. The neurostimulation system of claim 1, wherein the data acquisition unit is in communication with the neural electrode for recording the neuronal activity of the subject during the gait movement.

4. The neurostimulation system of claim 1, wherein the data acquisition unit communicates with the processor via a wireless network.

5. The neurostimulation system of claim 1, further comprising a stimulus generator wherein the processor outputs the stimulation signal to the neural electrode via the stimulus generator.

6. The neurostimulation system of claim 1, wherein the processor outputs the stimulation signal to the neural electrode continuously until the processor determines that the abnormal motor movement no longer exists.

7. A method of modulating an abnormal motor movement of a subject suffering from spinocerebellar ataxia, the method comprising:
   generating, using a processor, an EMG pattern based on a detected EMG signal, the detected EMG signal is generated in a muscle of the subject during a gait movement of the subject and is detected by an EMG electrode
   detecting, using a neural electrode implanted in a deep cerebellar nuclei of the subject, neuronal activity of the subject during the gait movement of the subject;
   synchronizing the EMG pattern with the neuronal activity detected by the neural electrode;
   generating, using the processor, a gait cycle based on the synchronized EMG pattern and neuronal activity;
   comparing, using the processor, the gait cycle with pre-set gait cycle data to determine the presence of abnormal motor movement associated with spinocerebellar ataxia in the subject; and
   upon determining presence of the abnormal motor movement, outputting, using the processor, a stimulation signal to the neural electrode to deliver a pulse to the deep cerebellar nuclei of the subject thereby modulating the abnormal motor movement associated with spinocerebellar ataxia in the subject.

8. The method of claim 7, wherein more than one EMG electrode is implanted in the muscle, and the muscle comprises tibialis anterior and/or gastrocnemius muscle.

9. The method of claim 7, wherein the processor includes a field-programmable gate array.

10. The method of claim 7, wherein a data acquisition unit is in communication with the neural electrode for recording the detected neuronal activity of the subject during the gait movement.

11. The method of claim 7, wherein the data acquisition unit communicates with the processor via a wireless network.

12. The method of claim 7, wherein the processor outputs the stimulation signal to the neural electrode via a stimulus generator.

13. The method of claim 7, wherein the processor outputs the stimulation signal to the neural electrode continuously until the processor determines that the abnormal motor movement no longer exists.

14. The method of claim 7, further comprising implanting the EMG electrode in the subject.

15. The method of claim 7, further comprising implanting the neural electrode in the deep cerebellar nuclei of the subject.

* * * * *